(12) United States Patent
 Niazi (10) Patent No.: US 9,200,335 B2
(45) Date of Patent: Dec. 1, 2015

(54) SEPARATIVE BIOREACTOR

(71) Applicant: Sarfaraz K. Niazi, Deerfield, IL (US)

(72) Inventor: Sarfaraz K. Niazi, Deerfield, IL (US)

(73) Assignee: Therapeutic Proteins International, LLC, Chicago, IL (US)

(*) Notice: Subject to any disclaimer, the term of this patent is extended or adjusted under 35 U.S.C. 154(b) by 97 days.

(21) Appl. No.: 14/186,974

(22) Filed: Feb. 21, 2014

(65) Prior Publication Data

US 2014/0170635 A1     Jun. 19, 2014

Related U.S. Application Data

(63) Continuation of application No. 13/092,955, filed on Apr. 24, 2011, now Pat. No. 8,668,886.

(51) Int. Cl.
| | |
|---|---|
| *B01J 8/00* | (2006.01) |
| *C12Q 3/00* | (2006.01) |
| *C12M 1/00* | (2006.01) |
| *C12M 1/12* | (2006.01) |
| *C12M 3/06* | (2006.01) |
| *C12M 1/34* | (2006.01) |

(52) U.S. Cl.
CPC .............. *C12Q 3/00* (2013.01); *C12M 23/14* (2013.01); *C12M 25/14* (2013.01); *C12M 27/16* (2013.01); *C12M 29/06* (2013.01); *C12M 41/32* (2013.01); *C12M 47/10* (2013.01); *Y10T 137/0318* (2015.04)

(58) Field of Classification Search
CPC ............................ C12M 23/14; B01F 11/0008
See application file for complete search history.

(56) References Cited

U.S. PATENT DOCUMENTS

| | | | | |
|---|---|---|---|---|
| 6,544,788 | B2 * | 4/2003 | Singh | 435/383 |
| 7,682,823 | B1 * | 3/2010 | Runyon | 435/305.2 |

* cited by examiner

*Primary Examiner* — Jyoti Nagpaul
(74) *Attorney, Agent, or Firm* — Therapeutic Proteins International, LLC; Cheryl Liljestrand (57) ABSTRACT

A bioreactor that combines the steps of recombinant expression and separation of a biological product by binding the secreted biological product with a resin, discarding the nutrient medium and eluting the biological product as a concentrated solution, eliminating the steps of sterile filtration and volume reduction. The method also allows loading of resin for column-purification, eliminating all steps of perfusion process and maintaining a sink condition of a toxic product in nutrient medium to optimize productivity of host cells. The instant invention also allows harvesting of solubilized inclusion bodies after the cells have been lysed and refolding of proteins inside the bioreactor.

17 Claims, 1 Drawing Sheet

SEPARATIVE BIOREACTOR

CROSS REFERENCE TO RELATED APPLICATION

This application is a continuation of U.S. patent application Ser. No. 13/092,955, entitled "SEPARATIVE BIOREACTOR" filed on Apr. 24, 2011, the contents of which are incorporated herein by reference in its entirety.

FIELD OF INVENTION

The instant invention relates to a bioreactor design intended to capture and purify biological products within the bioreactor.

BACKGROUND

The present invention relates to a novel bioreactor design for expressing and separating a biological product from other components in a bioreaction broth, which combines the step of expressing and separating within the bioreactor by binding the biological product with a resin within a bioreactor, discarding the nutrient medium and eluting the biological product as a concentrated solution; this allows elimination at least two steps in the separation and purification of biological products—filtration or centrifugation to remove cell culture and ultrafiltration for volume reduction—and possibly three steps, including loading of biological products on the purification columns.

For products which are expressed as inclusion bodies, the instant invention allows cell lysis, inclusion body solubilization and protein refolding within the bioreactor.

The instant invention significantly reduces the process time and cost while enhancing the yield by reducing degradation of biological products during manufacturing; additional benefits of the instant invention include avoiding perfusion process and reducing toxicity of the expressed biological products to cell culture. No such invention exists in the prior art of bioreactors.

Downstream processing involves steps for cleaning up crude biological products to yield high purity products. Traditionally, these steps involve using chromatography columns packed with highly specialized resins to capture and purify the desired biological products by the process of elution. With an exponential rise in the number of biological products being developed and marketed, there have been remarkable developments in the field of downstream processing; these have however not caught up with the developments in the upstream processing. A few years ago, an yield of 0.25 G of biological product per liter expressed by CHO cells was considered very high; today, we are hovering yields around 10 G/L making it possible to accumulate a very large quantity of biological products, particularly as the sizes of bioreactors have increased to thousands of liters. There are three steps that connect the upstream and downstream processing. First, the culture media must be filtered using fine filters (e.g., 0.22 microns) to remove cells (CHO cells have average size of 5 microns). This step utilizes an array of filters since the cells are likely to choke the filter surface easily and also require installing vessels that would receive the filtrate. This requires vessels of thousands of liters of capacity to match the size of the bioreactors. The next step is the reduction of the volume of filtrate since it is not possible to load such large volumes on columns that have limited flow rate. This is the stage where most often a cross-flow type filtration is used, again with a large bank of filters to complete the concentration process as quickly as possible. The mechanism of cross flow filtration place severe pressure on the solution and causes breakdown and precipitation of biological products resulting in losses of generally 10-20% at this stage. Both of these processes take a very long time and during this processing it is not possible to keep the biological product solution at a lower temperature resulting in the degradation of biological product as well. The third step is to load the concentrated solution in a chromatography column containing a binding media, a specific resin with affinity for the target biological product. Even though the volume of liquid has been reduced considerably at this stage, the loading steps, nevertheless, takes substantial time to complete the loading.

The time and cost-consuming steps of filtration, chromatography and purification slow down the manufacturing process and add substantial capital cost requirement to establish cGMP-grade manufacturing operations.

Bioreactors used in the upstream processing are vessels that allow growth of cell culture to express biological products and for reasons historic and traditional, a clear demarcation line exists between the expression of biological product and its purification. For this reason, no innovations have been made to add additional functions to the design of bioreactors while they do provide a large investment in a vessel that could possibly have multiple uses.

There is a large unmet need to stream line the entire process of biological manufacturing of products where the cost of manufacturing can be reduced substantially but combining several traditional steps in a single vessel, the bioreactor.

The instant invention discloses an innovative bioreactor design that accomplishes this goal and is applicable universally to all types of bioreaction applications.

SUMMARY OF INVENTION

There two major types of recombinant expressions of biological products, one is the soluble form of biological product that is secreted into nutrient medium by the cells as most often seen in the use of Chinese Hamster Ovary cells and the other is the retention of biological product inside the cell forming an inclusion body, as most often seen in the case of using *E. coli* for expression. Recent advances in genetic engineering have been able to encode the genes of bacteria that would secrete soluble proteins instead of retain them inside as inclusion bodies. This is to avoid the cumbersome process of cell-lysis and inclusion body solubilization.

Historically, biological products expressed in nutrient medium are separated from the medium by first removing the biological culture by a process of centrifugation or filtration. This step is followed by reducing the volume of medium to about ¹⁄₁₀ to ¹⁄₂₀ to make it possible to load the liquid within a reasonable time on purification columns. While these process steps have been widely validated and function very well, the practicality of using these steps becomes very difficult when large volumes of medium is handled.

Today, it is not uncommon to see bioreactors processing thousands and even hundreds of thousands of liters of medium at a time. To accommodate this, companies use very large-scale filtration and volume reduction methods that cost millions of dollars to install and millions more to operate and maintain. There is a very large unmet need to simplify these processes, reduce the cost of production and make the technology accessible to thousands of researchers and smaller companies who cannot afford such large investments. Circumventing these process hurdles would also make it possible to produce drugs based on these biological drugs cheaper to manufacture and thus increase their affordability to billions of people around the world who are not able to afford these drugs.

The key to the instant invention lies in following a contrarian teaching. While all manufacturers follow the path described above involving removal of components from a broth ready for purification, it would be prudent to examine the utility of first removing the target biological product instead and discarding what is not needed, instead of removing step by step what is not needed, as currently practiced.

The instant invention capitalizes on the recent availability of many resins that are capable of binding biological products in large quantities. Most modern resins would bind between 20-125 mg of biological product per mL of resin. Many of these resins are highly specific to the biological products and many of them can be combined to remove any type and quantity of a biological product from a solution by a simple process of physicochemical binding that is strong enough to retain the biological products attached to the resin while the culture medium is removed from the bioreactor. The art has also advanced significantly in the field of biological product purification wherein we now have a much better ability to elute these bound biological products from resins by adjusting the pH, the ionic strength or other characteristics of the eluting buffer to break the binding between the resin and the biological product. This allows removal of biological products from a bioreactor as a highly concentrated solution that is ready for further purification and in some instances it can even be the final product for use.

The bioreactor design of the instant invention is novel, and overcomes the most significant hurdles in the manufacture of biological products by applying a contrarian teaching in the current method of the manufacture of these products.

DETAILED DESCRIPTION OF INVENTION

Affinity Chromatography is a separation technique based upon molecular conformation, which frequently utilizes application specific resins. These resins have ligands attached to their surfaces, which are specific for the compounds to be separated. Most frequently, these ligands function in a fashion similar to that of antibody-antigen interactions. This "lock and key" fit between the ligand and its target compound makes it highly specific.

Many membrane proteins are glycobiological products and can be purified by lectin affinity chromatography. Detergent-solubilized proteins can be allowed to bind to a chromatography resin that has been modified to have a covalently attached lectin. Immunoaffinity chromatography resin employs the specific binding of an antibody to the target biological product to selectively purify the biological product. The procedure involves immobilizing an antibody to a column material, which then selectively binds the biological product, while everything else flows through.

Inclusion bodies upon solubilization exposes hydrophobic groups while there remain chemical groups on denatured proteins capable of binding to resin (Singh and Panda, 2005), allowed separation of these proteins during the stages of refolding to native state.

Some of the state of the art resins binding technologies include: Novozymes's newly patented Dual Affinity Polypeptide technology platform replaces Protein A process steps with similar, but disposable, technology; stimuli responsive polymers enable complexation and manipulation of biological products and allow for control of polymer and biological product complex solubility, which results in the direct capture of the product without centrifuges or Protein A media, from Millipore Corp.; mixed mode sorbents to replace traditional Protein A and ion exchange, for improved selectivity and capacity with shorter residence times. These media, with novel chemistries, include hydrophobic charge induction chromatography, such as MEP, and Q and S HyperCel from Pall Corp.; monoliths, involving chromatography medium as a single-piece homogeneous column, such as Convective Interaction Media monolithic columns from BIA Separations; simulated moving beds, involving multicolumn countercurrent chromatography, such as BioSMB from Tarpon Biosystems; Protein G (multiple vendors); single domain camel-derived (camelid) antibodies to IgG, such as CaptureSelect from BAC; new inorganic ligands, including synthetic dyes, such as Mabsorbent A1P and A2P from Prometic Biosciences; expanded bed adsorption chromatography systems, such as the Rhobust platform from Upfront Chromatography; ultra-durable zirconia oxide-bound affinity ligand chromatography media from ZirChrom Separations; Fc-receptor mimetic ligand from Tecnoge; ADSEPT (ADvanced SEParation Technology) from Nysa Membrane Technologies; membrane affinity purification system from PurePharm Technologies; custom-designed peptidic ligands for affinity chromatography from Prometic Biosciences, Dyax, and others; Protein A- and G-coated magnetic beads, such as from Invitrogen/Dynal; new affinity purification methods based on expression of biological products or MAbs as fusion biological products with removable portion (tag) having affinity for chromatography media, such as histidine) tags licensed by Roche (Genentech); Protein A alternatives in development, including reverse micelles (liposomes), liquid-liquid extraction systems, crystallization, immobilized metal affinity chromatography, and novel membrane chromatography systems; plug-and-play solutions with disposable components (e.g., ReadyToProcess), process development AKTA with design of experiments capability, and multicolumn continuous capture, from GE Healthcare.

It is surprising that while great advances have been made in the design of resins available to capture biological products, these have been only used in the downstream processing of purification. Adding resins to a crude mixture of biological products and host cells would be no different than the current process that simply concentrates the same medium and loads it onto columns. The only difference would be that when practiced at the end of the bioreaction cycle, this would require sufficient resin to bind almost the entire biological product. Assuming that a cell line produces 1 G/L of protein and the binding capacity is 0.1 G/mL, this will require 10 L of resin when operating a 1000 L bioreactor. When operating the instant invention to replace a perfusion system or continuously remove the biological product, smaller quantities of resins are required as they can be removed from the bioreactor and reused. However, if we examine the lifecycle of resins, the total cost of resin use would still be the same. With the cost of resins dropping substantially and the possibility of using non-specific binding resins reduces the cost burden of processing the entire yield at one time. The cost savings in the instant invention comes in the reduced time of approximately 50% in processing, allowing manufacturers to prepare a larger number of batches reducing the cost or production.

Additionally, one embodiment of the invention may be practiced by using the least expensive resins to generically bind all soluble organic components and then elute them instantly using a buffer without any concern for the profile of elution to separate these components. Such generic resins are very inexpensive and may not even have to be reused.

The instant invention offers four methods of biological product manufacturing and purification. The first method is the separation of a biological product at the end of the bioreaction cycle; the second method is the removal of biological product continuously while the resin remains inside the bioreactor and the third method involved periodically removing the resin and processing it outside the bioreactor. In the fourth method, the cells are lysed to expose inclusion bodies, which are then solubilized prior to contacting them with resin.

The first method would be the most commonly practiced art; the second method would be needed to obviate the toxic effects of expressed biological products and to replace a perfusion bioreaction method and the third method would be practiced when the biological product may not be stable in the complex stage or where it is desired to re-use the resin (particularly where the cost of the resin is high). The fourth method would be useful for bacterial expressions that involve formation of inclusion bodies and while newer constructs allow expression of soluble products, there remain a large number of existing methods that inevitably require handing inclusion bodies.

One of the main objectives of the instant invention is to eliminate certain unit processes, which are cumbersome and expensive, the instant invention introduces a concept of filtering out biological culture used in the bioreaction. Most bacteria would be about 8.mu. in diameter and the Chinese Hamster Ovary cells about 5.mu. in diameter. The binding resin is separated from the culture broth by a container device (pouch) that is porous and the porosity of the walls of the container is kept at below 5.mu. to prevent entry of any organism or cell into and contacting the resin. This prevents any physical adsorption of cells or organisms on the resin and fouling it. Additionally, during the drain cycle, when the liquid content of the bioreactor is drained, this removes all cells and organisms. Of course, any components of lysed cells or organisms would indeed enter the pouch and contact with the resin and will be retained by the resin. But this too is a process that is common with the present practice. In some instances, it may be necessary to use the pouches with larger diameter of 30.mu. or higher and this may cause some deposition of cells on the resin. For such instances, the invention adds an optional step of filtering the buffer eluted through a sterilizing filter to remove any remaining cells that might elute along with the biological product and those that may have remained attached to the resin during the wash cycle. But this stage of filtration will be much less cumbersome as smaller volumes are filtered with essentially 95% or more reduction in the filtration load and the risk of clogging of the filter since most of the culture has already been drained. For example, instead of filtering a 2000 L culture media to remove CHO cells, this will require filtering about 100 L or less; the cost and time savings would still be high. It is noteworthy that the downstream processes are required to remove host cell and DNA biological products effectively; current methods start with a substantial load of these biological products despite the filtration of the cells, so the instant invention does not add any new burden on the complexity of downstream processing.

Another most significant advantage of the methods disclosed comes in increased production yields. It is well established that the process of filtration, which is conducted under high pressure, inevitably decomposes biological products. By avoiding the filtration steps, it is envisioned that the product yields will improve substantially.

The very nature of the recombinant product makes it unstable. The instability of a recombinant biological product can be either physical or chemical. Physical instability can be related to such things as denaturation of the secondary and tertiary structure of the biological product, adsorption of the biological product onto interfaces or excipients, and aggregation and precipitation of the biological product. Chemical instability of a biological product results in the formation of a new chemical entity by cleavage or by new bond formation. Examples of this type of instability would be deamidation, proteolysis and racemization. Any changes to the manufacturing process that reduce the cycle of production, exposure to harsh conditions such as high pressures across membranes in cross-flow and sterile filtration, etc., would increase the stability and the final yield of production. In one method of batch processing, the biological products are harvested at the end of the cycle that might be as long as several weeks of continuous expression; while many biological products would survive the 37 C environment for that length of time, a few would degrade over period of time. By capturing the biological products through formation of resin-biological product complex, the stability of and thus the yield of production can be increased since in the complex stage, the molecules are immobilized and thus less likely to degrade. While many biological products may degrade by adsorbing to various surfaces, the interaction between a resin and biological product is of a different nature as evidenced by the use of resins in the purification of biological products whereby high degree of stability is maintained when eluting from a resin column.

Another most significant advantage of the methods disclosed here comes in reducing the toxicity of the biological products expressed to the cell lines expressing them; one may place the resin inside the pouch from the very beginning of the reaction process and as biological product is expressed, it is instantly captured by the resin removing from direct contact with the cell lines increasing their productivity and the longevity of expression cycle, decreasing the production costs substantially.

In a biological system, a particular biological product is expressed only in a specific subcellular location, tissue or cell type, during a defined time period, and at a particular quantity level. This is the spatial, temporal, and quantitative expression. Recombinant biological product expression often introduces a foreign biological product in a host cell and expresses the biological product at levels significantly higher than the physiological level of the biological product in its native host and at the time the biological product is not needed. The over-expressed recombinant biological product will perform certain function in the host cell if the biological product is expressed soluble and functional. The function of the expressed recombinant biological product is often not needed by the host cell. In fact the function of the biological product may be detrimental to the proliferation and differentiation of the host cell. The observed phenotypes of the host cells are slow growth rate and low cell density. In some cases, the recombinant biological product causes death of the host cell. These phenomena are described as biological product toxicity. These recombinant biological products are called toxic biological products.

Biological product toxicity is a commonly observed phenomenon. All active biological products will perform certain functions. The host cells need all of these functions with few exceptions and therefore they interfere with cellular proliferation and differentiation. The appeared phenotype of the effects of these biological products to the host cells is their "toxicity". It is estimated that about 80% of all soluble biological products have certain degree of toxicity to their hosts. About 10% of all biological products are highly toxic to host cells. The completely insoluble or dysfunctional biological products will not be toxic to the host cell, though they may drain the cellular energy to produce them when over-expressed. Biological product over-expression creates metabolic burden for the host cell, but this burden is not toxicity to the cell. Some low solubility or partially functional biological products may still be toxic to the host. While the exposure of the host cell to biological product being expressed is inevitable and is only optimized through codon usage, once the biological product has been expressed, it would be prudent to transport it out of the cell as soon as possible and this diffusion reaction requires establishing a sink condition that is readily achieved if the expressed biological product in the surroundings of the host cell is removed from the solution such as in the case of the instant invention by binding to a resin.

In another situation, where a perfusion system is used for the upstream production of recombinant biological products, a portion of culture media is replaced with fresh media and the media removed is filtered of host cells, reduced in volume and either stored at a lower temperature or processed with downstream processing. Still another most significant advantage of the method disclosed here comes in performing a perfusion bioreaction. The traditional process of perfusion can be replaced by simply removing the biological product from the solution by adding a resin to the pouch and replenishing any nutrients that may have been lost due to adsorption onto the resin. There is a substantial cost reduction in using this substitute method.

It is noteworthy that the instant invention allows for provisions to keep the bioreaction going at its optimal conditions by replenishing any nutrients lost to the binding resin; this may happen when the resins used have a non-specific binding characteristics. Where highly specific affinity binding resins are used, this step may be obviated or reduced in its frequency.

And yet another advantage of the disclosed method is that the final resin-biological product conjugate can be loaded directly column and eluted accordingly to specified protocols without first flushing it out with a buffer to break the bonding between the resin and the biological product. This will save substantial time and material savings.

A remarkable application of the instant invention is made in the manufacturing of recombinant biological products using bacterial culture. E. coli has been most widely used for the production of recombinant proteins that do not require posttranslational modifications such as glycosylation for bioactivity. A typical process involves, harvesting bacteria by a process of centrifugation, to collect the cell paste. Since the high-level expression of recombinant proteins results in accumulation of protein as insoluble aggregates as inclusion bodies, the cells are lysed, most commonly by a sonication process and the inclusion bodies solubilized (by the use of a high concentration of denaturants such as urea or guanidine hydrochloride, along with reducing agents such as beta-mercaptoethanol), refolded (by slow removal of the denaturant in the presence of oxidizing agent) and purified to recover functionality of the active product. Protein solubilization from the inclusion body using high concentration of chaotropic reagents results in the loss of secondary structure leading to the random coil formation of the protein structure and exposure of hydrophobic surface, a feature that is of significant importance in the instant invention.

One embodiment of the instant invention combines several procedures of cell lysis, solubilization and refolding into one continuous operation that can all be completed within the bioreactor, obviating the need for multiple vessels, handing large volumes of liquids and reducing process time and cost of manufacturing.

Protein production in *Escherichia coli* involves high-level expression in a culture, followed by harvesting of the cells and finally their disruption, or lysis, to release the expressed proteins. One of the most crucial steps to be optimized in the protein production process is bacterial cell lysis. Although bacterial cell lysis does not influence protein expression, it can have an effect on protein solubility by affecting the physicochemical properties of the protein. Chemical lysis can be achieved by using different buffer composition, lysozyme, or commercially available detergent reagents. Cell lysis can also include a combination of the mechanical and chemical lysis, e.g., lysozyme with freeze-thaw cycles. The preferred method, or "gold standard", for bacterial lysis on the small or standard laboratory scale production is sonication. It relies on the mechanical disruption of the bacterial cell wall. Any solubilizing lysis agents, like detergents, that can affect solubility or stability, do not affect the expressed protein. Sonication becomes more problematic when handling large volumes of culture media. For these reasons, many high throughput laboratories choose to optimize lysis conditions by chemical means.

Chemical lysis includes the treatment of cells with alkali, enzyme, or detergents. Chemical lysis methods minimize denaturation and expose the inner, cytoplastmic membrane by degrading the peptidoglycan cell wall of bacteria. The cell wall of Gram-positive bacteria is thick, containing several interconnecting layers of peptidoglycan (60-90% of the cell was). In contrast the cell wall of Gram-negative bacteria appears thin, containing two or three layers of peptigoglycan (10-20%) of the cell wall). In addition to this, Gram-negative bacteria contain an outer membrane composed of lipopolysaccharide, phospholipids, and lipoprotein. Lysozyme, a commercial lytic enzyme, is widely used to lyse Gram-positive cells in the presence of EDTA and detergent Brij 58. Lysozyme hydrolyzes N-acetylmuramide linkages, resulting in degradation of bacterial cell walls. The activity of lysozyme is optimal in the pH range of 6.7 to 8.6.

In contrast, gram-negative bacteria are less susceptible to lysozyme and detergents due to the presence of asymmetric lipid bilayer. The outer membrane of the peptidoglycan acts as a permeability barrier to large molecules, and so the outer membrane needs to be permeabilized to expose the peptidoglycan layer for successful enzymatic lysis. The permeability barrier is, in part, due to the presence of polyanionic lipopolysaccharide that provide a network interaction in the presence of divalent cations, such as $Mg^{2+}$. The chelators of divalent carions (e.g., EDTA), polycationic species, and small molecules (e.g., Tris) are suitable for permeabilizing the membrane in order to release lipopolysachccharides.

Chemical cell lysis can be performed using lysis solution containing either lysozyme (Sigma-Aldrich, St. Louis, Mo.), SoluLyse® in Tris buffer (Genlantis, San Diego, Calif.) or Bugbuster® protein extraction reagent (Novagen, EMD Chemicals Inc., San Diego, Calif.). The amount of soluble protein and the percentage recovered in the soluble fraction using SoluLyse® well correlates with sonication. Compositions and protocols for chemical lysis are widely available through commercial suppliers of chemical lysis products. The quantity of various chemicals used, the time of exposure and determination of the end point are readily established for any specific process.

Solubilizing the lysed cell product would yield a denatured protein with large hydrophobic and ionic surfaces that can be readily bound to resins like cationic, anionic or hydrophobic resins; in some instances, certain solution characteristics like the pH, ionic strength of polarity may have to be adjusted to achieve optimal binding to the resin introduced in the pouch. This will allow discarding of the large volume of liquid culture medium and cell debris; it is noteworthy that the pore size of the pouch would generally be small enough to exclude cell lysis debris to contact the resin.

The solubilized proteins bound to resins can then be removed from the binding and a solution of protein allowed to refold inside the bioreactor and again once the refolding has been completed, binding the proteins to resin and discarding the refolding solution obviating the need for expensive and time consuming cross-flow filtration operations. The concentrated solutions of refolded proteins are then subjected to further purification.

There remains a large unmet need to develop a technology wherein the target biological product is selectively or non-selectively removed from the culture media prior to subjecting it to customary purification processes. The instant invention, taking a contrarian approach, is targeted to modify the existing designs of bioreactors to include a step of performing biological product harvesting or biological product capturing prior to purification chromatography steps to increase the throughput of manufacturing processing without adding expensive and technically challenging modifications.

The key component of the instant invention lies in a feature added to a traditional bioreactor, whether a hard-walled system or a flexible disposable system. A pouch made of a porous material (likely a polymeric or metallic mesh) with porosity that is smaller than the size of resin used to capture biological products is used to allow contacting of the resin with the biological product. Most resins come in sizes ranging from 50 microns and up; some have smaller particle size as well. However, it is possible to design a pouch, a bag or a container form a polymeric material such as nylon that would keep the resin within the bag and not allow it to enter to the culture medium when the pouch is placed inside a bioreactor. To make sure that smaller particles of the resin are not flushed out of the bag carrying biological products with them, it would be necessary to sort out the resin first by placing it in a similar bag as installed in a bioreactor and immersing it in water to flush out any smaller particles. It is noteworthy that the resins, though expensive, can be re-used numerous times without losing their efficacy of binding and even when they do, the method descried here allows for adjusting the quantity of resin to achieve maximum capture of biological products.

A significant advancement in the art of biological product capture is provided here by disclosing that a mixture of resins can be used to obviate the binding of sites on the resin by other functional groups found in the culture media. The ultimate goal is to design a mixture of resins that would always capture the all of the biological products in the culture medium within the shortest period of time. Once used, the resins can be cleansed, sanitized and readied for the next use. It is important to know that there is no need for sterilizing these resins as long as they are treated chemically to reduce the microbial load.

Recent advances in the sensors available for bioreactors now make it possible to monitor many properties including dissolved oxygen, dissolved carbon dioxide, electrolyte concentration, pH, turbidity, cell count, temperature, and also the concentration of dissolved biological products, all by using non-invasive methods. The instant invention can be automated by installing such sensors and more particularly a sensor to determine concentration of the biological product so that the resin can be added to the pouch at a certain time when the concentration of the biological product in culture media has reached a pre-determined high level and allowing it to equilibrate until such time that the concentration in the culture media decreases to a certain pre-determined low level, most likely below 1% of the highest level prior to the treatment with resin.

Common Embodiments

In a first embodiment, the instant invention proposes a bioreactor capable of growing all types of cells and organisms and additionally provides a ready means of harvesting of biological products in a bioreactor. The instant invention employs a mechanical device, which in one step combines several steps or biological product harvesting. The method of the present invention presents a novel procedural step for simultaneously extracting and concentrating a biological product of interest from a host cell, at the same time removing practically all, or at least the majority of the host cell biological products.

In a second embodiment, the present invention relates to a bioreactor that contains a resin capable of binding target biological products but kept separate from the culture medium by placing it inside a pouch that has porous walls with pores small enough to hold the resin inside the pouch yet allow the culture media containing target biological product to freely equilibrate with the resin. By placing the resin in a pouch, several arduous step in protein harvesting are avoided. It is the purpose of this invention to work the purification process in an opposite order to how the art is currently practiced universally. In all instances, upon the completion of the bioreaction, the first step is to remove the host cells or organisms by filtration or centrifugation. With the bioreactor volumes into thousands of liters, this process is extremely arduous, expensive and requires additional storage vessels of about the same size as the bioreactor making it difficult to accommodate these processes in smaller facilities. A goal of this invention is to reverse the process and instead of removing the host cells and organisms, remove the biological product first. This modification also eliminates the need to reduce the volume of filtrate received after removing the host cells and organisms in the traditional process prior to purification. To accomplish this, the bioreactor contains a pouch that is filled with a resin when the process is ready for harvesting, allowing equilibration of the binding process and the draining out the culture media along with host cells and organisms. The drainage is best accomplished by allowing the culture media to flow down under gravity, thus obviating any steps that might take a long time like peristaltic pumping of the culture medium out of the bioreactors. The biological product is eluted using a buffer that causes breakdown of the association between the biological product and the resin and collecting a concentrated solution. Prior to contacting the resin-biological product complex with a buffer, the complex can be washed if necessary with fluids that would not break down the resin-biological product complex but remove other components bound to resin that may have come from the metabolic products in the culture media. Just in case there are any host cells remaining, this solution, which would be about 2-5% of the volume of the culture media, can be easily filtered through a sterilizing filter.

In a third embodiment, the instant invention obviates the need for costly cross-flow filtration processes used in every type of manufacturing of biological products as in almost all instances a concentration step is involved to reduce the volume of liquid that is loaded onto purification column. The purification of biological therapeutics generally involves the use of cross flow filtration (tangential flow filtration), normal flow filtration (dead ended filtration) combined with chromatographic separations. Cross flow filtration and normal flow filtration retain matter through size exclusion and are complementary to chromatography's selectivity. For processes where volumes are large such as into thousands of liters, the cost of equipment for filtration is into hundreds of thousands of dollars with expensive filters all adding to a cost that represents a major fraction of the total cost of manufacturing of recombinant drugs.

In a fourth embodiment, the instant invention provides a means of continuously removing expressed biological product from a culture media to enhance the level of expression that may be depressed because of the higher concentration of biological product in the mixture. The instant invention allows maintenance of a sink condition for the concentration of the biological product at all times.

In a fifth embodiment, the instant invention provides a means of continuously removing expressed biological product from a culture media to reduce the toxicity of the expressed biological product to host cells and thus prolonging the cycles of expression substantially increasing the yields of production.

In a sixth embodiment, the instant invention provides a means of increasing the chemical stability of expressed biological product by binding it to a resin as soon as it is expressed as the chemicals are always less stable in a solution form than in a solid form or in this case a complex form; this would substantially improve the yield of production.

In a seventh embodiment, the instant invention provides a means of substantially reducing the cost of recombinant drug manufacturing by eliminating some of the most costly and time consuming steps. The cost of using a non-specific resin is minimal as this can be used repeatedly unlike the resin used in the downstream purification where it must be replaced periodically as it loses its power to resolve the separation. Until the resin breaks down or is physically damaged, it can be used continuously and even when the efficiency of adsorption is reduced, it can be mixed with fresh resin to give it a very long useful life.

In an eight embodiment, the instant invention combines several steps of upstream and downstream bioprocessing; in the harvesting process, the resin-biological product complex can be directly treated with buffers to begin the first stage of purification and where the resin is carefully and artfully selected, lead to high purity of a biological product in one step. The resin-biological product complex is ready for downstream processing without the need to load a column intended for downstream processing and this can save substantial time for loading; the prolonged delay in loading columns as currently practiced is often detrimental to the stability of target biological product; this can be avoided using the instant invention.

In a ninth embodiment, the instant invention offers to eliminate a very laborious and expensive step of first stage filtration or other means of separating the biological product harvested; by using a pouch to contain the resin, all steps generally required to remove resin such as decanting, centrifugation (low speed), filtration (coarse) can be avoided altogether; the pouches can be stringed together so that these are simply removed by picking up the end of the string at one end. The pouches can also be then packed directly in a column for elution as if this were loose resin. Since the pouches containing the resin can be pre-washed to remove the resin of particle size smaller than the porosity of the filter that forms the pouch, the losses of bound biological product to resin will be eliminated. The pouches can be washed and re-used, perhaps requiring a sterilization step if these are used during the bioreaction cycle, a chemical can achieve the sterilization similar to what is used in the sanitization of the chromatography column. This method of holding the resin in a pouch further reduces any loss of resin and saves additional costs.

In a tenth embodiment, the instant invention describes a novel method of biological product purification wherein all those steps which are expensive and time consuming are obviated; the method of biological product purification involves adding to a solution of biological product ready for purification, a resin contained in a pouch that is the first resin to be used in the process of purification. Once the biological product binds completely to the resin, the resin is packed into a purification column. This method of loading the biological product in a purification column is more efficient than the traditional method of calculating the capacity of binding of resin and thus determining the volume of resin used. There are always possibilities of miscalculations since the binding of the biological product to the resin is dependent on many factors, most important, the physicochemical characteristics of the liquid loaded—this characteristics would vary in every batch, the calculations of the amount of resin required are at best good theoretical guesses. Loading too much protein would cause of loss of protein and adding too little, add to the cost of resin. The instant invention allows for a perfect match of the binding capacity to the quantity of the biological product bound, as it is possible to monitor the concentration of the unbound concentration of the biological product. Once the quantity of resin used is such that the concentration of the biological product in the nutrient medium is reduced to a pre-determined level, it is assumed that all protein has been bound.

In an eleventh embodiment, the instant invention provides a method of extraction of solubilized inclusion bodies by lysing the cells in the bioreactor, solubilizing the inclusion bodies and capturing them with a resin to remove them from the bioreactor. This application substantially reduces the cost of manufacturing of proteins, which are expressed as inclusion bodies.

The overall impact of these embodiments is quantifiable in terms of the time it takes to make a biological product ready for purification; as a general guideline, if a 2000 L batch of a recombinant production is ready for processing, it will take about 10-12 hours to filter it through a 0.22.mu. micron filter to remove host cells such as Chinese Hamster Ovary Cells; this step would then be followed by a cross-flow filtration process that might take 12-24 hours to reduce the volume to 200-300 liters; this step is then followed by loading on the column, which may take another 6-24 hours depending on the size of the column used. While the batch is subjected to above processes, the target biological product is under going degradation, both because of the effects of temperature as well as the strain exerted on biological products in the filtration process. The instant invention offers a solution to replace all of these steps with a single short step with a time savings of at least 50% in the overall process time and material savings of about 30% and improved yields of about 20%.

Bioreactor Design

Figure 1:
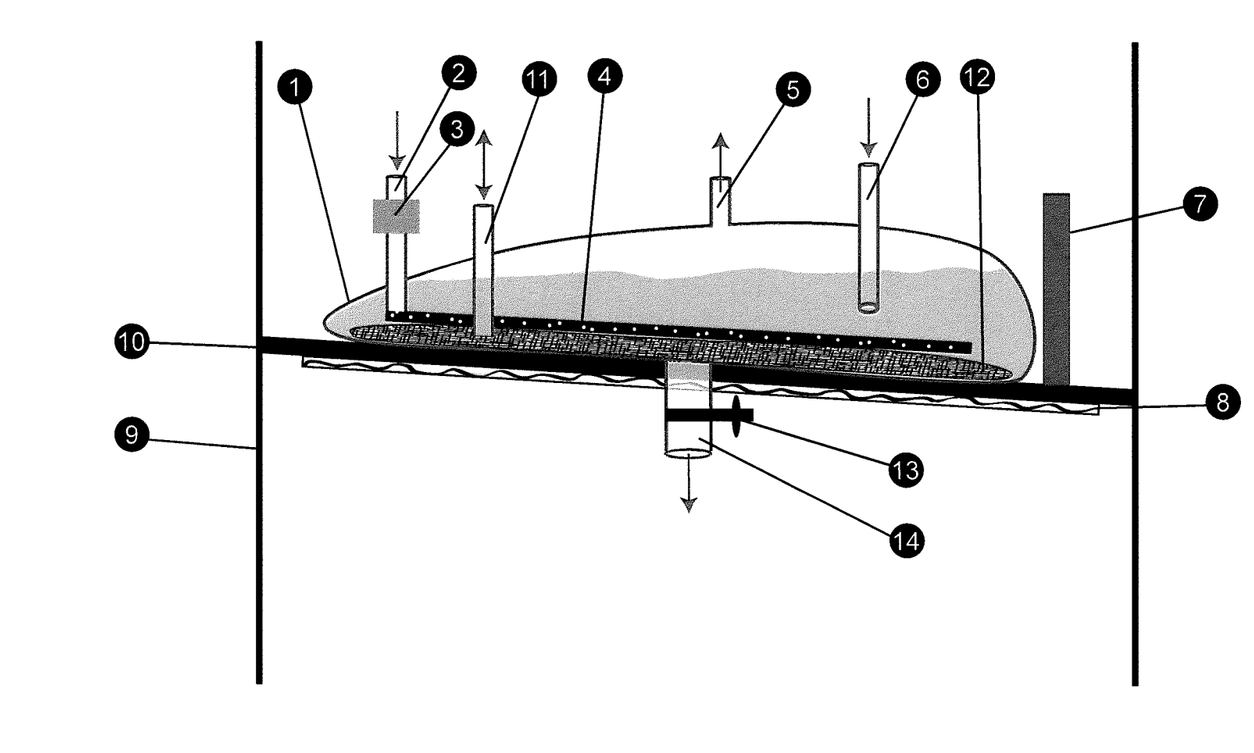
FIG. 1. A flexible two-dimensional disposable bioreactor displaying the installation of the pouch used for adding resin to the bioreactor to separate the biological products form the bioreactor.

FIG. 1 shows a preferred embodiment of the invention. The bioreactor consists of a two dimensional disposable flexible bag (1) resting on a support surface (10), which is capable of being tilted and further resting on a frame (9), a means of gassing consisting of a gas inlet (2), a gas filter (3) and a sparging tube (4). The flexible bag (1) further contains a gas outlet (5), a nutrient medium inlet (6), a liquid drain (14) controllable by a stopcock (13), a means of heating (8) the support surface (10) a means of agitating the nutrient medium comprising a flapper (7) that compresses on the flexible bag (1) intermittently; also provided in the preferred embodiment of the invention is a pouch (12) with a resin inlet/outlet (11) to add or remove the resin.

The above-preferred embodiment of a bioreactor design would be useful in the manufacture of all types of biological products using all types of cells and organisms. The bioreactor is operated by first adding a fixed volume of a nutrient medium to the flexible bag, which would generally be supplied, pre-sterilized by gamma radiation. The nutrient medium may be sterile filtered directly into the bag for convenience. The bag would rest on a supportive surface that can be tilted if needed. Generally, for bag sizes of up to 36 inches, this may not be necessary; otherwise the support surface can be raised on one side by an angle of 0.1 to 5 degrees. This slight tilt of the supportive surface adds potential energy to the nutrient medium and causes it to draw more towards the flapper (7). The flapper mechanism is turned on resulting in the flapper compressing on the flexile bag at one end of the bag. This compression produces a wave inside the bag that travels to the other end of the bag and then returns after striking the other end of the bag; a slight tilt, if utilized, assures that there is no accumulation of unmixed media at the other end of the bag opposite to the end of bag being compressed periodically. The flapper would generally be operated at a rate of 25-60 rpm depending on the volume of nutrient medium, and the size of the bag used. Generally, the flexible bag would be filled to about 60% of the capacity. Once the flapper mechanism has begun operating and the mixing seems adequate as evidenced by smooth moving of nutrient medium inside the bag, the heating element (8) is turned on to achieve a desire temperature inside the bag. Sensors may be attached to the bag to record the temperature and connect these sensors to a feedback heating mechanism that would assure maintenance of an appropriate temperature such as 37 C. These sensors are not shown in FIG. 1 as they are customary and generically available. Alternately, a sample of nutrient medium may be drawn to measure its characteristics. Once the temperature reaches the desired level, a biological culture of a recombinant organism such as Chinese Hamster Ovary cell or *E. coli* would be added to the nutrient medium through the nutrient medium inlet and the bag allowed mixing. Alternately, the biological culture may be added at any time, even before adding the nutrient medium. The gas is turned on to begin sparging of the nutrient medium at a rate predetermined to be suitable for the specific process. For an *E. coli* expression experiment, the flow rate would be approximately 0.8 to 1 vvm of compressed air. The key to achieving best aeration and the highest KLA value is to allow the bag to inflate only slightly, to allow sufficient surface for the sparged air to escape, yet not cause pressurization of the bag. It is for this reason that the air outlet is carefully controlled for the outlet rate. Once a steady state of flow rate, bag pressurization and mixing dynamics is achieved, the bioreactor is allowed to run, such as overnight when using for bacterial fermentation or for several days when using Chinese Hamster Ovary cells. During this period, the nutrient medium may be fed with nutrients through the media inlet tube. The optical density of bacterial culture or the cell density, dissolved oxygen and pH can be carefully monitored to assure the optimal condition for the expression of biological products in the nutrient medium. While the preferred embodiment would function only when the biological product is present in a solution form in nutrient medium, the biological processes that produce an inclusion body can also benefit from the instant invention if the cells are chemically lysed and the inclusion bodies solubilized. It is now well established in prior art that solubilized inclusion bodies can be loaded onto resin columns to perform refolding of proteins and thus there exist a large number of resins that would quickly and efficiently bind solubilized inclusion bodies. Thus the instant invention is applicable to bacterial production even if they do not directly express soluble proteins. However, the process of manufacture of the biological products would involve a chemical treatment to lyse the cells and then chemically solubilize the inclusion bodies prior to moving to the resin-binding step.

The next step is to calculate the amount of resin needed to bind the biological product based on the concentration of the biological product in the nutrient medium. The resin is first prepared by removing resin particles that would be smaller than the pore size of the pouch (which would generally be about 3.mu.). The sized resin is then introduced directly into the pouch through the pouch inlet and the nutrient medium allowed to agitate while the gassing is turned off. [It is expected that more than 99.9% of all resins used would have particle size larger than 3.mu. and thus no bleeding of resin will take place back into bioreactor}. Samples of nutrient medium are taken periodically to ascertain when the majority of the biological product has become bound to the resin inside the pouch. Generally, this would be above 90% reduction in the concentration of the biological product in the nutrient medium. It may be necessary to add more resin if the concentration of the biological product does not reach a pre-determined low level within a pre-determined time. The time needed for such equilibration will be about 20-30 minutes; however, specific binding rate studies would need to be conducted to assure that an optimal minimal time is allowed for such equilibration.

Once it is determined that an optimal binding of the biological product has been achieved, the drain port is operated by opening the stopcock and the culture media along with cells or organisms is allowed to flow out under gravity force. For large-scale operations, it may be necessary to install the drain port towards one end of the bag and the bag tilted to force fast removal of the nutrient medium from the bag. The utilization of gravity flow is a major energy and time saving feature. In those instances where thousands of liters of nutrient media is used, any mechanical process for moving or handling nutrient media would be an inefficient process compared to gravity flow resulting in discarding of nutrient media. It is further emphasized that the NIH guidelines for LSGP (large scale good practice) allow many recombinant cells to be directly discarded into sewer without any treatment as they are not infectious; this is particularly true of the Chinese Hamster Ovary Cells that comprise the largest production engine in bioprocessing. Even some *E. coli* bacteria are exempted from any decontamination step. In such situations, the most energy and cost efficient process is draining of nutrient media directly into sewer. The size of the drain would have to match with the flow rate desired and where large volumes are used, several drains can be installed in the bioreactor to quickly and efficiently remove nutrient medium. Once the nutrient medium has been drained out, the stopcock in the drain is closed. At this stage, the manufacturer would have two options, one is to fill the bag with a buffer that would not cause the breaking of the binding between the biological product and the resin but would be generally effective in removing other smaller molecular weight components that might have become attached to the resin. The bag would then be agitated for a brief period of time and the buffer (which may even be water) drained out again by turning on the stopcock in the drain port. This would be the washing step. This step can be skipped and the bag filled with a buffer solution that would cause the breakdown of the binding between the biological product and the resin; this would generally require a pH adjustment, a polarity adjustment and an electrolyte adjustment. These conditions would have already been worked out in the early phases of process development. Once the breaking or eluting buffer is allowed to react within the bag, the biological product would be released into the buffer solution, which can be monitored for the concentration of the biological product to assure that a desirable recovery has been achieved. While the goal is to recover almost the entire biological product, it may at times be more useful to settle with a more practical level of recovery such as 90 to 95%. Once this stage has reached, turning on the stopcock again opens the drain port and the concentrated solution of the biological product is collected in a microbiologically clean vessel. Generally, the volume of the solution will be about 2-5% of the original nutrient medium. This concentrated solution would then be transferred to downstream purification columns. In most instances, it may be desirable to pass this concentrated solution through a sterilizing filter to remove any cells that might have been carried over to prevent the blocking of the purification columns. It is expected that the titer of cells at this stage will be very small allowing use of simpler and faster filtration methods and even if the solution is not filtered, the chance of blocking the purification column would be minimal. Smart manufacturing processes have the fewest steps involved; the manufacturers would be advised to consider eliminating this filtration step if possible.

In another preferred embodiment, the bioreactor is operated as provided in the embodiment above, except that the resin is added in the beginning of the bioreaction cycle to bind the biological product as it is expressed in the nutrient medium. This technique would then not be applicable to situations where the biological product is expressed as inclusion bodies. Smaller portions of resins are added periodically to the pouch in quantities just enough to bind the expressed biological product. This is necessary to prevent blockage of binding sites on the resin by other adsorbable materials in the nutrient medium, and to minimize the losses of nutrient elements to the resin, which should be replenished periodically. This method would be analogous to a traditional perfusion system except that the steps to replace the media, filtering it and replacing media with fresh media are obviated. This method is also a useful method to reduce the toxicity of the biological product to the host cells expressing the biological product. This method would work well for those biological products that can stay stable when bound to resin as the complex between the biological product and the resin is kept in the pouch until the end of the bioraction cycle.

In another preferred embodiment, a further improvement is made in the preceding embodiment where the resin is added periodically. In this practice of the method, the resin is first removed that has become equilibrated with the biological product prior to adding fresh resin; this allows the removal of biological products bound to resin and avoids any instability problems due to keeping the conjugate of biological product and resin in the bioreactor for a prolonged time. The resin is removed readily by inserting a tube from the inlet/outlet to the pouch, which would generally be of a cylindrical shape and aspirating the resin, using vacuum. It is noteworthy that the size of the tube inserted is such that it fits snugly inside the tubular (cylindrical) pouch pushing the resin as the tube goes down and forcing the resin into the tube by mechanical displacement. Once the tube has settled down deep into the pouch, a vacuum is applied carefully avoiding aspirating any substantial quantities of the nutrient medium. The resin collected periodically can be kept at a more suitable temperature and combined at an appropriate time or processed individually.

In another preferred embodiment, a further application is provided to bioreaction systems wherein the biological product is expressed inside the cell as an inclusion body. The bioreactor is operated as described above but instead of monitoring the concentration of biological product, the optical density of the biological culture is monitored. When a predetermined optical density is reached, the bioreaction process is stopped, the cells lysed chemically and the resultant inclusion bodies solubilized, all inside the bioreactor. Once a suitable solubilization of the inclusion body has been achieved, an appropriate mixture of resins is added to bind the solubilized inclusion bodies. The rest of the method is then followed for the separation of the nutrient medium, detachment of solubilized inclusion bodies from the resin and further purification. It is further noted that there may not be a need for further filtration to remove cells, as they would all have been lysed. In some instances, the protein can be refolded within the bioreactor using appropriate refolding buffer after detaching the solubilized inclusion bodies from the resin. The bioreactor container offers a remarkable opportunity to extend the use to refold proteins eliminating the need for operating another vessel. It is almost ironic that in general practice, the volume of the refolding solution is generally equal to the nutrient medium, making the bioreactor and ideal choice for protein refolding.

In another preferred embodiment, a further utility of the instant invention is provided wherein the operation of bioreactor as described above produces a mixture of the biological product and the resin and this complex can be directly loaded into chromatography purification columns avoiding another cumbersome and time-consuming step.

Generally, the invention provides bioreactors and methods, which are universal in the sense that the invention is suitable and adaptable for processing a variety of compositions, including both biologic and non-biologic components. Indeed, an inventive bioreactor designed for use with mammalian cells, for example, may be used for culturing bacteria, allowing ease of manufacturing.

As used herein, the term "liquid" is intended to encompass compositions, which include biologic components as described herein.

Compositions comprising non-biologic components include, but are not limited to, those which comprise microcarriers (e.g., polymer spheres, solid spheres, gelatinous particles, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, cells, capillaries, and aggregates (e.g., aggregates of cells).

The biological components that may be processed in accordance with the invention are described in the paragraphs which follow and include, but are not limited to, cell cultures derived from sources such as animals (e.g., hamsters, mice, pigs, rabbits, dogs, fish, shrimp, nematodes, and humans), insects (e.g., moths and butterflies), plants (e.g., algae, corn, tomato, rice, wheat, barley, alfalfa, sugarcane, soybean, potato, lettuce, lupine, tobacco, rapeseed (canola), sunflower, turnip, beet cane molasses, seeds, safflower, and peanuts), bacteria, fungi, and yeast.

Illustrative animal cells include Chinese hamster ovary (CHO), mouse myeloma, M0035 (NSO cell line), hybridomas (e.g., B-lymphocyte cells fused with myeloma tumor cells), baby hamster kidney (BHK), monkey COS, African green monkey kidney epithelial (VERO), mouse embryo fibroblasts (NIH-3T3), mouse connective tissue fibroblasts (L929), bovine aorta endothelial (BAE-1), mouse myeloma lymphoblastoid-like (NSO), mouse B-cell lymphoma lymphoblastoid (WEHI 231), mouse lymphoma lymphoblastoid (YAC 1), mouse fibroblast (LS), hepatic mouse (e.g., MC/9, NCTC clone 1469), and hepatic rat cells (e.g., ARL-6, BRL3A, H4S, Phi 1 (from Fu5 cells)).

Illustrative human cells include retinal cells (PER-C6), embryonic kidney cells (HEK-293), lung fibroblasts (MRC-5), cervix epithelial cells (HELA), diploid fibroblasts (WI38), kidney epithelial cells (HEK 293), liver epithelial cells (HEPG2), lymphoma lymphoblastoid cells (Namalwa), leukemia lymphoblastoid-like cells (HL60), myeloma lymphoblastoid cells (U 266B1), neuroblastoma neuroblasts (SH-SY5Y), diploid cell strain cells (e.g., propagation of poliomyelitis virus), pancreatic islet cells, embryonic stem cells (hES), human mesenchymal stem cells (MSCs, which can be differentiated to osteogenic, chondrogenic, tenogenic, myogenic, adipogenic, and marrow stromal lineages, for example), human neural stem cells (NSC), human histiocytic lymphoma lymphoblastoid cells (U937), and human hepatic cells such as WRL68 (from embryo cells), PLC/PRF/5 (i.e., containing hepatitis B sequences), Hep3B (i.e., producing plasma proteins: fibrinogen, alpha-fetoprotein, transferrin, albumin, complement C3 and/or alpha-2-macroglobulin), and HepG2 (i.e., producing plasma proteins: prothrombin, antithrombin III, alpha-fetoprotein, complement C3, and/or fibrinogen).

Cells from insects (e.g., baculovirus and *Spodoptera frugiperda* ovary (Sf21 cells produce Sf9 line)) and cells from plants or food, may also be cultured in accordance with the invention. Cells from sources such as rice (e.g., *Oryza sativa*, *Oryza sativa* cv Bengal callus culture, and *Oryza sativa* cv Taipei 309), soybean (e.g., *Glycine max* cv Williams 82), tomato (*Lycopersicum esculentum* cv Seokwang), and tobacco leaves (e.g., *Agrobacterium tumefaciens* including Bright Yellow 2 (BY-2), *Nicotiana tabacum* cv NT-1, *N. tabacum* cv BY-2, and *N. tabacum* cv Petite Havana SR-1) are illustrative examples.

Bacteria, fungi, or yeast may also be cultured in accordance with the invention. Illustrative bacteria include *Salmonella, Escherichia coli, Vibrio cholerae, Bacillus subtilis, Streptomyces, Pseudomonas fluorescens, Pseudomonas putida, Pseudomonas* sp, *Rhodococcus* sp, *Streptomyces* sp, and *Alcaligenes* sp. Fungal cells can be cultured from species such as *Aspergillus niger* and *Trichoderma reesei*, and yeast cells can include cells from *Hansenula polymorpha, Pichia pastoris, Saccharomyces cerevisiae, S. cerevisiae* crossed with *S. bayanus, S. cerevisiae* crossed with LAC4 and LAC-.sub.1-2 genes from *K. lactis, S. cerevisiae* crossed with *Aspergillus shirousamii, Bacillus subtilis, Saccharomyces diastasicus, Schwanniomyces occidentalis, S. cerevisiae* with genes from *Pichia stipitis*, and *Schizosaccharomyces pombe.*

A variety of different products may also be produced in accordance with the invention. Illustrative products include proteins (e.g., antibodies and enzymes), vaccines, viral products, hormones, immunoregulators, metabolites, fatty acids, vitamins, drugs, antibiotics, cells, and tissues. Non-limiting examples of proteins include human tissue plasminogen activators (tPA), blood coagulation factors, growth factors (e.g., cytokines, including interferons and chemokines), adhesion molecules, Bcl-2 family of proteins, polyhedrin proteins, human serum albumin, scFv antibody fragment, human erythropoietin, mouse monoclonal heavy chain 7, mouse IgGn.sub.2b/k, mouse IgG1, heavy chain mAb, Bryondin 1, human interleukin-2, human interleukin-4, ricin, human .alpha.1-antitrypisin, biscFv antibody fragment, immunoglobulins, human granulocyte, stimulating factor (hGM-CSF), hepatitis B surface antigen (HBsAg), human lysozyme, IL-12, and mAb against HBsAg. Examples of plasma proteins include fibrinogen, alpha-fetoprotein, transferrin, albumin, complement C3 and alpha-2-macroglobulin, prothrombin, antithrombin III, alpha-fetoprotein, complement C3 and fibrinogen, insulin, hepatitis B surface antigen, urate oxidase, glucagon, granulocyte-macrophage colony stimulating factor, hirudin/desirudin, angiostatin, elastase inhibitor, endostatin, epidermal growth factor analog, insulin-like growth factor-1, kallikrein inhibitor, .alpha.1-antitrypsin, tumor necrosis factor, collagen protein domains (but not whole collagen glycoproteins), proteins without metabolic byproducts, human albumin, bovine albumin, thrombomodulin, transferrin, factor VIII for hemophilia A (i.e., from CHO or BHK cells), factor VIIa (i.e., from BHK), factor IX for hemophilia B (i.e., from CHO), human-secreted alkaline phosphatase, aprotinin, histamine, leukotrienes, IgE receptors, N-acetylglucosaminyltransferase-III, and antihemophilic factor VIII.

Enzymes may be produced from a variety of sources using the invention. Non-limiting examples of such enzymes include YepACT-AMY-ACT-X24 hybrid enzyme from yeast, *Aspergillus oryzae* .alpha.-amylase, xylanases, urokinase, tissue plasminogen activator (rt-PA), bovine chymosin, glucocerebrosidase (therapeutic enzyme for Gaucher's disease, from CHO), lactase, trypsin, aprotinin, human lactoferrin, lysozyme, and oleosines.

Vaccines also may be produced using the invention. Non-limiting examples include vaccines for prostate cancer, human papilloma virus, viral influenza, trivalent hemagglutinin influenza, AIDS, HIV, malaria, anthrax, bacterial meningitis, chicken pox, cholera, diphtheria, haemophilus influenza type B, hepatitis A, hepatitis B, pertussis, plague, pneumococcal pneumonia, polio, rabies, human-rabies, tetanus, typhoid fever, yellow fever, veterinary-FMD, New Castle's Disease, foot and mouth disease, DNA, Venezuelan equine encephalitis virus, cancer (colon cancer) vaccines (i.e., prophylactic or therapeutic), MMR (measles, mumps, rubella), yellow fever, Haemophilus influenzae (Hib), DTP (diphtheria and tetanus vaccines, with pertussis subunit), vaccines linked to polysaccharides (e.g., Hib, *Neisseria meningococcus*), *Staphylococcus pneumoniae*, nicotine, multiple sclerosis, bovine spongiform encephalopathy (mad cow disease), IgG1 (phosphonate ester), IgM (neuropeptide hapten), SIgA/G (*Streptococcus mutans* adhesin), scFv-bryodin 1 immunotoxin (CD-40), IgG (HSV), LSC (HSV), Norwalk virus, human cytomegalovirus, rotavirus, respiratory syncytial virus F, insulin-dependent autoimmune mellitus diabetes, diarrhea, rhinovirus, herpes simplex virus, and personalized cancer vaccines, e.g., for lymphoma treatment (i.e., in injectable, oral, or edible forms). Recombinant subunit vaccines also may be produced, such as hepatitis B virus envelope protein, rabies virus glycoprotein, *E. coli* heat labile enterotoxin, Norwalk virus capsid protein, diabetes autoantigen, cholera toxin B subunit, cholera toxin B an dA2 subunits, rotavirus enterotoxin and enterotoxigenic *E. coli*, fimbrial antigen fusion, and porcine transmissible gastroenteritis virus glycoprotein S.

Viral products also may be produced. Non-limiting examples of viral products include sindbis, VSV, oncoma, hepatitis A, channel cat fish virus, RSV, corona virus, FMDV, rabies, polio, reo virus, measles, and mumps.

Hormones also may be produced using the invention. Non-limiting examples of hormones include growth hormone (e.g., human growth hormone (hGH) and bovine growth hormone), growth factors, beta and gamma interferon, vascular endothelial growth factor (VEGF), somatostatin, platelet-derived growth factor (PDGF), follicle stimulating hormone (FSH), luteinizing hormone, human chorionic hormone, and erythropoietin.

Immunoregulators also may be produced. Non-limiting examples of immunoregulators include interferons (e.g., beta-interferon (for multiple sclerosis), alpha-interferon, and gamma-interferon) and interleukins (such as IL-2).

Metabolites (e.g., shikonin and paclitaxel) and fatty acids (i.e., including straight-chain (e.g., adipic acid, Azelaic acid, 2-hydroxy acids), branched-chain (e.g., 10-methyl octadecanoic acid and retinoic acid), ring-including fatty acids (e.g., coronaric acid and lipoic acid), and complex fatty acids (e.g., fatty acyl-CoA)) also may be produced.

The containers useful in the various embodiments of the invention may be of any size suitable for containing a liquid. For example, the container may have a volume between 1-40 L, 40-100 L, 100-200 L, 200-300 L, 300-500 L, 500-750 L, 750-1,000 L, 1,000-2,000 L, 2,000-5,000 L, or 5,000-10,000 L. In some instances, the container has a volume greater than 1 L, or in other instances, greater than 10 L, 20 L, 40 L, 100 L, 200 L, 500 L, or 1,000 L. Volumes greater than 10,000 L are also possible. Preferably, the container volume will range between about 1 L and 1000 L, and more preferably between about 5 L and 500 L, and even more preferably between 5 L and 200 L.

The components of the bioreactors and other devices described herein which come into contact with the culture medium or products provided thereby desirably comprise biocompatible materials, more desirably biocompatible polymers, and are preferably sterilizable.

It should also be understood that many of the components described herein also are desirably flexible, e.g., the containers desirably comprise flexible biocompatible polymer containers (such as collapsible bags), with the conduits also desirably comprising such biocompatible polymers. The flexible material is further desirably one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. If desired, portions of the flexible container may comprise a substantially rigid material such as a rigid polymer (e.g., high density polyethylene), metal, and/or glass.

Desirably the containers comprise biocompatible materials, more desirably biocompatible polymers. When collapsible containers are selected for use, the container may be supported by or may line an inner surface of a support structure, e.g., the outer support housing having container-retaining sidewalls. However, the invention may be practiced using non-collapsible or rigid containers or conduits.

The containers may have any thickness suitable for retaining the culture medium therewithin, and may be designed to have a certain resistance to puncturing during operation or while being handled. For example, the walls of a container may have a total thickness of less than or equal to 250 mils (1 mil is 25.4 micrometers), less than or equal to 200 mils, less than or equal to 100 mils, less than or equal to 70 mils (1 mil is 25.4 micrometers), less than or equal to 50 mils, less than or equal to 25 mils, less than or equal to 15 mils, or less than or equal to 10 mils. In certain embodiments, the container may include more than one layer of material that may be laminated together or otherwise attached to one another to impart certain properties to the container. For instance, one layer may be formed of a material that is substantially oxygen impermeable. Another layer may be formed of a material to impart strength to the container. Yet another layer may be included to impart chemical resistance to fluid that may be contained in the container.

It thus should be understood that a container may be formed of any suitable combinations of layers. The container (e.g., collapsible bag) may include, for example, 1 layer, greater than or equal to 2 layers, greater than or equal to 3 layers, or greater than equal to 5 layers of material(s). Each layer may have a thickness of, for example, less than or equal to 200 mils, less than or equal to 100 mils, less than or equal to 50 mils, less than or equal to 25 mils, less than or equal to 15 mils, less than or equal to 10 mils, less than or equal to 5 mils, or less than or equal to 3 mils, or combinations thereof.

In addition, the container preferably is seamless in order to improve its strength and avoid deposition of growing cells in the media.

All or portions of the container also are desirably translucent, or more desirably transparent, to allow viewing of contents inside the container. The latter is preferred when it is desirable to irradiate the culture medium within the container.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

PRIOR ART

The instant invention is type of separative bioreactor. In the past substantial progress has been made in membrane bioreactors (MBR) that had the ability to separate the products within the bioreactors. The MBR process was introduced by the late 1960s, as soon as commercial scale ultrafiltration (UF) and microfiltration (MF) membranes were available. The original process was introduced by Dorr-Olivier Inc. and combined the use of an activated sludge bioreactor with a cross-flow membrane filtration loop. The flat sheet membranes used in this process were polymeric and featured pore sizes ranging from 0.003 to 0.01 .mu.m. Although the idea of replacing the settling tank of the conventional activated sludge process was attractive, it was difficult to justify the use of such a process because of the high cost of membranes, low economic value of the product (tertiary effluent) and the potential rapid loss of performance due to membrane fouling. As a result, the focus was on the attainment of high fluxes, and it was therefore necessary to pump the mixed liquor suspended solids (MLSS) at high cross-flow velocity at significant energy penalty (of the order 10 kWh/m3 product) to reduce fouling. Due to the poor economics of the first generation MBRs, they only found applications in niche areas with special needs like isolated trailer parks or ski resorts for example. The breakthrough for the MBR came in 1989 with the idea of Yamamoto and co-workers to submerge the membranes in the bioreactor. Until then, MBRs were designed with the separation device located external to the reactor (side-stream MBR) and relied on high transmembrane pressure (TMP) to maintain filtration. With the membrane directly immersed into the bioreactor, submerged MBR systems are usually preferred to sidestream configuration, especially for domestic wastewater treatment. The submerged configuration relies on coarse bubble aeration to produce mixing and limit fouling. The energy demand of the submerged system can be up to 2 orders of magnitude lower than that of the sidestream systems and submerged systems operate at a lower flux, demanding more membrane area. In submerged configurations, aeration is considered as one of the major parameter on process performances both hydraulic and biological. Aeration maintains solids in suspension, scours the membrane surface and provides oxygen to the biomass, leading to a better biodegradability and cell synthesis.

The other key steps in the recent MBR development were the acceptance of modest fluxes (25% or less of those in the first generation), and the idea to use two-phase bubbly flow to control fouling. The lower operating cost obtained with the submerged configuration along with the steady decrease in the membrane cost encouraged an exponential increase in MBR plant installations from the mid 90s. Since then, further improvements in the MBR design and operation have been introduced and incorporated into larger plants. While early MBRs were operated at solid retention times (SRT) as high as 100 days with mixed liquor suspended solids up to 30 g/L, the recent trend is to apply lower solid retention times (around 10-20 days), resulting in more manageable mixed liquor suspended solids (MLSS) levels (10-15 g/L). Thanks to these new operating conditions, the oxygen transfer and the pumping cost in the MBR have tended to decrease and overall maintenance has been simplified. There is now a range of MBR systems commercially available, most of which use submerged membranes although some external modules are available; these external systems also use two-phase flow for fouling control. Typical hydraulic retention times (HRT) range between 3 and 10 hours. In terms of membrane configurations, mainly hollow fiber and flat sheet membranes are applied for MBR applications.

Despite the more favorable energy usage of submerged membranes, there continued to be a market for the side stream configuration, particularly in industrial applications. For ease of maintenance the side stream configuration can be installed at low level in a plant building. Membrane replacement can be undertaken without specialist equipment, and intensive cleaning of individual banks can be undertaken during normal operation of the other banks and without removing the membranes modules from the installation.

As a result research continued with the side stream configuration, during which time it was found that full-scale plants could be operated with higher fluxes. This has culminated in recent years with the development of low energy systems which incorporate more sophisticated control of the operating parameters coupled with periodic back washes, which enable sustainable operation at energy usage as low as 0.3 kWh/m3 product.

Argonne scientists (www.anl.gov) recently used electrical force to transport organic acids away from the biocatalyst across an ion-exchange membrane and into a concentrate chamber, very similar to normal metabolism processes for handling acids. To provide the electricity in a cost efficient fashion, researchers turned to electrodeionization (EDI). EDI is an established commercial technology for producing high-purity water. Previously, Argonne scientists modified EDI so that it could be used for desalination of chemical and agricultural products. To accomplish this, researchers molded loose ion exchange resin beads into a porous resin wafer, enabling the capture of charge salts and acids at dilution levels with high-energy efficiency and significantly reduced waste streams compared to conventional processing. This became the basis for the Argonne's separative bioreactor. Researchers also realized that although direct enzyme immobilization on membranes provided excellent product separations, insufficient enzyme density limited the overall performance. In order to increase the density, the scientists integrated enzyme immobilization technology into the porous resin wafer and created a material that can efficiently produce and remove organic acids. As Argonne designed its separative bioreactor, researchers incorporated enzyme capture resin beads into the resin wafer. Sugars were converted by the immobilized biocatalyst to the target acids, and the product was electrically transported into a concentrate channel. This resulted in reactions occurring without buffering or neutralization. Argonne's immobilization technology also allows in-situ stripping and replacement of degraded enzymes without disassembling the system. However, every type of membrane separative bioreactor disclosed utilized a similar principle of forcing a biological product across a membrane. The instant invention differs significantly by providing a device capable of containing a resin capable of binding the target biological product, the membrane holding the resin has no specific function except to keep the resin separated form the bulk liquid in the bioreactors and also to prevent larger scale organisms or cells to contact the resin. The separation function in the instant invention is provided by a non-specific, non-electrically driven reaction.

The prior art on the design and operation of separative bioreactors is silent on the concept of instant invention. The main references to separative bioreactors of use in biological sciences appear as U.S. patent application Ser. No. 10/9393, 642 file 19 Nov. 2004 wherein a separative bioreactor is disclosed. Accordingly, it is a separative bioreactor, comprising an anode and a cathode, a plurality of reaction chambers each having an inlet and an outlet and each including a porous solid ion exchange wafer having ion-exchange resins, each of the reaction chambers being interleaved between a cation exchange membrane and an anion exchange membrane or between either a cation or an anion exchange membrane and a bipolar exchange membrane, a plurality of product chambers each having an inlet and an outlet and separated from one of the reaction chambers by either a cation or an anion exchange membrane, recirculation mechanism for transporting material between the reaction chamber inlets and outlets and for transporting product between the product chamber inlets and outlets, and mechanism for supplying an electric potential between the anode and the cathode causing ions to be transported between chambers, whereby counterions retained or produced in each of the reaction chambers during the production of an ionizable organic product including product ions combine with oppositely charged ions to form molecules some or all of which are transported to reaction chamber inlets while product ions are transported into an adjacent product chamber to combine with oppositely charged ions to form product in a product stream exiting the product chamber outlets continuously recirculated to the product chamber inlets to increase the concentration of product in the product stream. None of the features described in this application are material to the instant invention and none of the essential features of the instant inventions are disclosed in this application.

The U.S. patent application Ser. No. 11/732,992 filed 5 Apr. 2007 discloses a porous solid ion exchange wafer comprising a combination of an biomolecule: capture-resin and an ion-exchange resin forming a charged capture resin containing a transition metal anion of +2 valence within said wafer. Additionally, this application claims a separative bioreactor, comprising an anode and a cathode, a plurality of reaction chambers at least some being formed from a porous solid ion exchange wafers having a combination of an biomolecule capture-resin and an ion-exchange resin forming a charged capture resin within said wafer and having a genetically tagged biomolecule immobilized on said charged capture resin, each of said porous solid ion exchange wafers having a charged capture resin therewithin being interleaved between a cation exchange membrane and an anion exchange membrane, and mechanism for supplying an electric potential between the anode and the cathode. None of these disclosures are common to the instant invention and the essential features of the instant invention are not recited in this application.

The U.S. Pat. No. 7,306,934 issued 11 Dec. 2007 discloses a porous solid ion exchange wafer for immobilizing biomolecules, said wafer comprising a combination of an biomolecule capture-resin containing a transition metal cation of +2 valence and an ion-exchange resin. The patent further discloses a separative bioreactor, comprising an anode and a cathode, a plurality of reaction chambers at least some being formed from a porous solid ion exchange wafers having a combination of art biomolecule capture-resin and an ion-exchange resin and having a genetically engineered tagged biomolecule immobilized on said biomolecule capture resin, each of said porous solid ion exchange wafers being interleaved between a cation exchange membrane and an anion exchange membrane, and mechanism for supplying an electric potential between the anode and the cathode. The instant invention does not rely on any features disclosed in this patent, nor any features of the instant invention are recited in this patent.

The U.S. Pat. No. 7,799,548 issued 21 Sep. 2011 is for a method of in situ stripping a genetically tagged biomolecule from a porous solid ion exchange wafer in a bioreactor, the wafer having a combination of a biomolecule capture-resin and an ion-exchange resin forming a charged capture resin within the wafer and having a genetically tagged biomolecule immobilized on said biomolecule capture-resin, comprising contacting the porous solid ion exchange wafer in the bioreactor with a stripping fluid at a temperature and for a time sufficient to strip at least some of the genetically tagged biomolecule therefrom. This patent additionally claims method of in situ stripping a genetically tagged biomolecule from a porous solid ion exchange wafer in a bioreactor and thereafter regenerating a genetically tagged biomolecule onto the porous solid ion exchange wafer, the wafer having a combination of a biomolecule capture-resin and an ion-exchange resin forming a charged capture resin within the wafer and having a genetically tagged biomolecule immobilized on said biomolecule capture-resin thereon, comprising contacting the porous solid ion exchange wafer in the bioreactor with a stripping fluid at a temperature and for a time sufficient to strip at least some of the genetically tagged biomolecules therefrom, and thereafter contacting the stripped porous solid ion exchange wafer in the bioreactor with an effective amount of a genetically tagged biomolecules at a temperature and for a time sufficient to immobilize genetically tagged biomolecules on the charged capture resin. The instant invention does not rely on any disclosures made in this patent nor are any of the essential features of the instant invention disclosed in this patent.

The U.S. Pat. No. 7,141,154 issued 28 Nov. 2006 discloses a method of continuously making an organic ester from a lower alcohol and an organic acid, comprising, introducing an organic acid or an organic salt into and/or producing an organic acid or an organic salt in an electrodeionization (EDI) stack having an anode and a cathode and a plurality of reaction chambers each formed from a porous solid ion exchange resin wafer interleaved between anion exchange membranes or an anion exchange membrane and a cation exchange membrane or an anion exchange membrane and a bipolar exchange membrane, providing mechanism for establishing an electric potential between the EDI anode and cathode, wherein at least some reaction chambers are esterification chambers and/or bioreactor chambers and/or chambers containing an organic acid or salt, whereby an organic acid or organic salt present in the EDI stack disassociates into a cation and an anion with the anion migrating into an associated esterification chamber through an anion exchange membrane if required and reacting with a lower alcohol in the esterification chamber to form an organic ester and water with at least some of the water splitting into a proton and a hydroxyl anion with at least some of the hydroxyl anion migrating to an adjacent chamber, said migration of ions being facilitated by establishing an electric potential across the EDI anode and cathode. The patent additionally discloses an apparatus for manufacturing an organic ester, comprising an electrodeionization (EDI) stack having an anode and a cathode and a plurality of reaction chambers each formed from a porous solid ion exchange resin wafer interleaved between anion exchange membranes or an anion exchange membrane and either a cation exchange membrane or a bipolar membrane, mechanism for establishing an electrical potential between said EDI anode and said cathode, at least some of said reaction chambers being esterification chambers or esterification chambers separated from an adjacent bioreactor chamber by an anion exchange membrane and/or an acid/base capture chamber, said bioreactor chambers each containing an ion exchange resin wafer capable of forming an organic acid or salt from an ionizable fluid flowing therein, said esterification chambers each containing an ion exchange resin wafer capable of forming an organic ester and water from a lower alcohol and an anion of an organic acid or salt, a source of anions supplied directly to said esterification chambers or supplied from adjacent chambers, and a supply of lower alcohol to said esterification chambers, whereby when a potential is established across said EDI anode and cathode at least some hydroxyl anions in said esterification chambers from water splitting migrate across said anion exchange membranes to adjacent chambers to drive the reaction to continuously produce an organic ester. None of the features disclosed in this patent are material to the instant invention and none of the essential features of the instant invention are disclosed or taught in this patent.

In summary, the prior art disclosed above teaches the use of porous solid ion exchange wafer for immobilizing biomolecules, said wafer comprising a combination of an biomolecule capture-resin containing a transition metal cation of +2 valence; it also teaches a separative bioreactor, comprising an anode and a cathode, a plurality of reaction chambers at least some being formed from a porous solid ion exchange wafers (above) having a combination of art biomolecule capture-resin and an ion-exchange resin and having a genetically engineered tagged biomolecule immobilized on said biomolecule capture resin, each of said porous solid ion exchange wafers being interleaved between a cation exchange membrane and an anion exchange membrane, and mechanism for supplying an electric potential between the anode and the cathode. The instant invention is significantly different from the separative bioreactor taught above. First, the instant invention does not require use of electrodes, or resins with a transition cation of +2 valence or immobilized metal ion affinity chromatography. The use of EDI (electrodeionization) and specific use of tags and limited nature of solvents to remove the captured biological products mainly enzymes makes this patent teachings distinctly different from the instant invention. In addition, and most significantly, the prior art can not be used with the preferred embodiment of the instant invention wherein flexible bioreactors are taught.

Moreover, the prior art requires additional hardware that adds substantial cost to the processing of manufacturing biological products while the instant invention combines several processes into one without adding any new cost element. The prior art is also specific to certain types of molecules while the instant invention is generic to every type of biological product.

What is claimed is:

1. A method for producing and separating a biological product from a liquid comprising:
   a. providing a separative bioreactor comprising:
      (1) a container suitable for growing a biological culture, wherein the container further comprises a liquid inlet and a drain; and
      (2) at least one pouch comprising a porous material with a plurality of pores and capable of housing a binding resin, wherein the pouch is placed inside the container, and wherein the pouch optionally comprises at least one resin inlet/outlet port directly connected to the pouch;
   b. introducing nutrient medium into the container;
   c. introducing biological culture into the container;
   d. growing of the biological culture by agitating the liquid;
   e. determining the concentration of biological product in the liquid at periodic intervals;
   f. introducing resin into the pouch, when the concentration of biological product reaches a desired amount, through the resin inlet sufficient to bind the biological product determined in step (e);
   g. determining the concentration of biological product in the liquid until it reaches a predetermined low value;
   h. removing the liquid from the container through the drain and discarding it; and
      (1) adding to the container a sufficient quantity of a buffer capable of removing the biological product from the resin and collecting the buffer for further purification of the biological product; or
      (2) removing the resin by aspirating the resin through the resin port and subjecting the resin to further steps of purification outside the container.

2. A method for producing and separating a biological product from a volume of liquid comprising:
   a. providing a separative bioreactor comprising:
      (1) a container suitable for growing a biological culture, wherein the container further comprises a liquid inlet and a drain; and
      (2) at least one pouch comprising a porous material with a plurality of pores and capable of housing a binding resin, wherein the pouch is placed inside the container, and wherein the pouch optionally comprises at least one resin inlet/outlet port directly connected to the pouch;
   b. introducing nutrient medium into the container;
   c. introducing biological culture into the container;
   d. growing of the biological culture by agitating the liquid;
   e. determining the concentration of biological product in the liquid at periodic intervals;
   f. introducing resin into the pouch at periodic intervals during growth of the biological culture through the resin inlet sufficient to bind the biological product determined in step (e);
   g. continue growth of the biological culture;
   h. continue binding of the biological product to the resin until the concentration of biological product in the liquid reaches a desired low value;
   i. removing the liquid from the container through the drain and discarding it; and
      (1) adding to the container a sufficient quantity of a buffer capable of removing the biological product from the resin and collecting the buffer for further purification; or
      (2) removing the resin by aspirating the resin through the resin port and subjecting the resin to further steps of purification outside the container.

3. A method for producing and separating a biological product from a volume of liquid comprising:
   a. providing a separative bioreactor comprising:
      (1) a container suitable for growing a biological culture, wherein the container further comprises a liquid inlet and a drain; and
      (2) at least one pouch comprising a porous material with a plurality of pores and capable of housing a binding resin, wherein the pouch is placed inside the container, and wherein the pouch optionally comprises at least one resin inlet/outlet port directly connected to the pouch;
   b. introducing nutrient medium into the container;
   c. introducing biological culture into the container;
   d. growing of the biological culture by agitating the liquid;
   e. determining the density of the biological culture in the liquid at periodic intervals;

f. when the density of the biological culture reaches a predetermined high value, adding to the liquid a chemical solution capable of lysing the cells to release inclusion bodies into the liquid;

g. adding to the liquid, a chemical solution capable of solubilizing the inclusion bodies;

h. adding sufficient quantity of a resin to the pouch to bind substantially all of the solubilized inclusion bodies;

i. removing the liquid from the container through the drain and discarding it; and
   (1) adding sufficient quantity of a chemical solution in the container to break the bond between the solubilized inclusion bodies and the resin and collecting the chemical solution containing solubilized inclusion bodies through the drain for further purification; or
   (2) removing the resin by aspirating the resin through the resin port.

4. The method of claim 3 further comprising:

a. adjusting the pH, electrolyte concentration and dielectric properties of the chemical solution in step (i)(1) to allow the inclusion bodies to release the biological product in a denatured form;

b. determining the concentration of the denatured biological product and adjusting the concentration of the biological product by adding water to the container to a predetermined low value;

c. adjusting the temperature of the chemical solution in step (b) to a predetermined level;

d. starting agitation at a predetermined low speed for a predetermined period of time to allow the denatured biological product to refold to its native state;

e. adding to the pouch a sufficient quantity of a resin capable of binding substantially all of the refolded biological product;

f. draining the chemical solution in step (e) through the drain and discarding it;

g. adding to the container a buffer capable of breaking the binding of the refolded biological product with resin;

h. collecting the buffer from step (g) through the drain for further purification.

5. The method of claim 3 further comprising:

a. placing the resin of step (i)(2) in a suitable container for purification of the biological product;

b. adding sufficient quantity of a chemical solution in the container to break the bond between the solubilized inclusion bodies and the resin and collecting the chemical solution containing solubilized inclusion bodies;

c. adjusting the pH, electrolyte concentration and dielectric properties of the chemical solution to allow the inclusion bodies to release the biological product in a denatured form;

d. determining the concentration of the denatured biological product and adjusting the concentration of the biological product by adding water to the container to a predetermined low value;

e. adjusting the temperature of the chemical solution in step (d) to a predetermined level;

f. starting agitation at a predetermined low speed for a predetermined period of time to allow the denatured biological product to refold to its native state;

g. adding a pouch comprising a sufficient quantity of a resin capable of binding substantially all of the refolded biological product;

h. removing the resin from the pouch and loading the resin in a chromatography column for further purification.

6. The method of any one of claims 1-3, wherein said biological product is selected from the group consisting of solubilized inclusion bodies, small proteins, enamel matrix proteins, fusion proteins, tag proteins, hormones, parathyroid hormones, growth hormones, gonadotropins, insulin, ACTH, prolactin, placental lactogen, melanocyte stimulating hormone, thyrotropin, calcitonin, enkephalin, angiotensin, cytokines human serum albumin, bovine serum albumin, ovalbumin, glucose isomerase, $\alpha$-amylase, endo-$\beta$-glucanase, growth hormone (GH), IGF-1, IGF-2, PTH, PGE2, TGF-$\beta$, TGF-$\alpha$, bEGF, EGF, PDGF-AB, PDGF-BB, osteoprotegerin (OPG), osteopontin (OP), FGF-1, FGF-2, thyroid hormone, BMP-2, BMP-3, BMP-4, BMP-6, BMP-7, VEGF, L25(OH)2, vitamin D3, caclitonin, IFN-gamma, OCN (osteocalcin), ON (osteonectin), OP-1 (osteogenic protein-1), NGF, collagen, fibronectin, fibrinogen, thrombin, factor XIII, a recombinant protein, a recombinant antibody and a recombinant peptide.

7. The method of any one of claims 1-3, wherein said biological product is an industrial biological product.

8. The method of any one of claims 1-3, wherein the nutrient medium is modified using procedures comprising pH adjustment, ionic strength adjustment and/or polarity adjustment to optimize binding of the biological product prior to adding the resin to the pouch.

9. The method of any one of claims 1-3, wherein said resin comprises an ionic-exchange resin, a hydrophobic resin, an affinity resin or a mixture thereof.

10. The method of any one of claims 1-3, wherein said resin comprises a mix-bed resin.

11. The method of any one of claims 1-3, wherein said resin comprises a Protein-A or Protein-G resin.

12. The method of any one of claims 1-3, wherein said resin comprises a resin with specific affinity towards said biological product.

13. The method of any one of claims 1-3, wherein said resin comprises a mixture of resins.

14. The method of any one of claims 1-3, wherein said resin is washed at least once prior to contacting with the buffer capable of breaking binding of biological product with resin.

15. The method of any one of claims 1-3, wherein nutrients are added periodically or continuously to replace any nutrients lost by binding to the resin.

16. The method of any one of claims 1-3, wherein the container further comprises a sparging filter capable of aerating the biological culture.

17. The method of any one of claims 1-3, wherein the container further comprising a heating element and a temperature controller for growing the biological culture at temperatures greater than ambient temperature.

* * * * *